(12) United States Patent
Markworth et al.

(10) Patent No.: US 6,660,006 B2
(45) Date of Patent: Dec. 9, 2003

(54) ROD PERSUADER

(75) Inventors: Aaron Markworth, Pompton Lakes, NJ (US); Yves Crozet, Ramsey, NJ (US)

(73) Assignee: Stryker Spine (FR)

( * ) Notice: Subject to any disclaimer, the term of this patent is extended or adjusted under 35 U.S.C. 154(b) by 0 days.

(21) Appl. No.: 10/124,170

(22) Filed: Apr. 17, 2002

(65) Prior Publication Data

US 2003/0199872 A1 Oct. 23, 2003

(51) Int. Cl.$^7$ .............................................. A61B 17/56
(52) U.S. Cl. ........................................................ 606/61
(58) Field of Search .......................... 606/61, 73, 99, 606/104

(56) References Cited

U.S. PATENT DOCUMENTS

| 5,020,519 | A |   | 6/1991  | Hayes et al. |        |
|-----------|---|---|---------|--------------|--------|
| 5,364,397 | A |   | 11/1994 | Hayes et al. |        |
| 5,449,361 | A | * | 9/1995  | Preissman    | 606/61 |
| 5,454,819 | A | * | 10/1995 | Knoepfler    | 606/147|
| 5,707,371 | A |   | 1/1998  | Metz-Stavenhagen |    |
| 5,720,751 | A | * | 2/1998  | Jackson      | 606/99 |
| 5,782,830 | A |   | 7/1998  | Farris       |        |
| 5,910,141 | A |   | 6/1999  | Morrison et al. |     |
| 6,036,692 | A |   | 3/2000  | Burel et al. |        |
| 6,066,143 | A | * | 5/2000  | Lane         | 606/72 |
| 6,123,707 | A |   | 9/2000  | Wagner       |        |
| 6,139,549 | A |   | 10/2000 | Keller       |        |
| 6,174,311 | B1|   | 1/2001  | Branch et al.|        |
| 6,183,472 | B1|   | 2/2001  | Lutz         |        |
| 6,261,296 | B1| * | 7/2001  | Aebi et al.  | 606/61 |
| 6,342,057 | B1|   | 1/2002  | Brace et al. |        |
| 6,379,364 | B1|   | 4/2002  | Brace et al. |        |
| 6,440,133 | B1| * | 8/2002  | Beale et al. | 606/99 |
| 6,440,142 | B1| * | 8/2002  | Ralph et al. | 606/99 |

* cited by examiner

Primary Examiner—David O. Reip
(74) Attorney, Agent, or Firm—Lerner, David, Littenberg, Krumholz & Mentlik, LLP

(57) ABSTRACT

An apparatus for persuading an orthopedic rod into position in an orthopedic device such as an implant or coupling element is disclosed. The apparatus includes a body, a pusher member and a trigger slidingly coupling the pusher member to the body. The pusher member includes a slide and sleeve attached to the slide. The sleeve includes at least one pusher bar. A ratchet controls the translation of the pusher member along the body to urge the rod into position in the orthopedic device. The pusher member and body define a cannula so that a fastener may be inserted once the rod is in position. The apparatus is operable via a single hand. In addition, a method of urging an orthopedic rod into a recess of an orthopedic device using the rod persuader is provided.

69 Claims, 10 Drawing Sheets

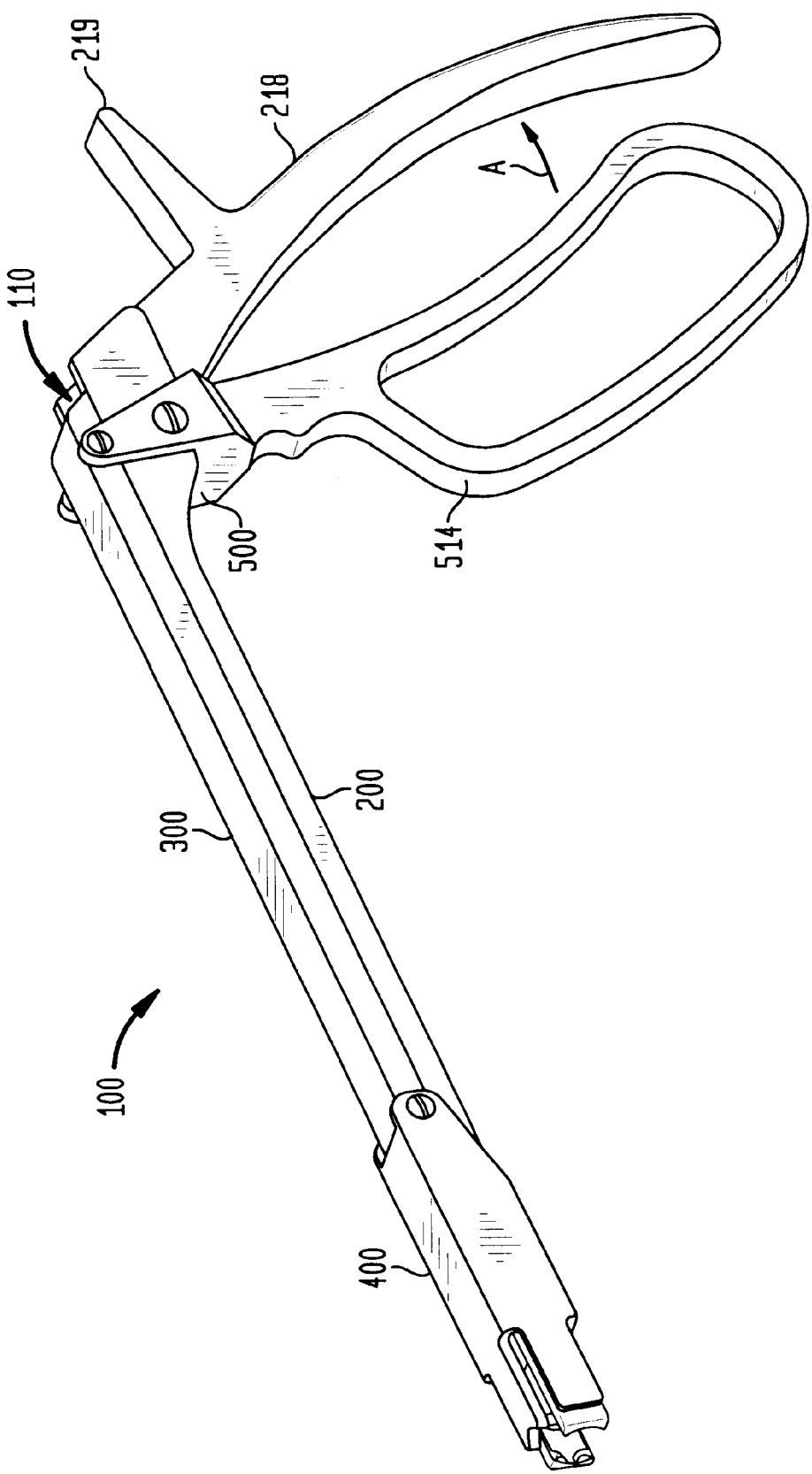

ROD PERSUADER

BACKGROUND OF THE INVENTION

The present invention relates to an instrument for urging an orthopedic rod into a recess in an orthopedic device and more particularly, to an instrument for securing a spinal rod to a coupling element.

The spinal column is a highly complex system of bones and connective tissues that provides support for the body and protects the delicate spinal cord and nerves. The spinal column includes a series of vertebral bodies stacked one atop the other, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord and nerves is located behind the vertebral bodies.

There are many types of spinal column disorders, including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease or trauma, such as ruptured or slipped discs, degenerative disc disease, fractured vertebra, and the like. Patients that suffer from such conditions usually experience extreme and debilitating pain, as well as diminished nerve function.

Surgical techniques commonly referred to as spinal fixation use surgical implants and/or mechanical immobilization to fuse two or more vertebral bodies of the spinal column. Spinal fixation may also be used to alter the alignment of adjacent vertebral bodies relative to one another so as to change the overall alignment of the spinal column. Such techniques have been used effectively to treat the above-described conditions and, in many cases, to relieve pain.

One spinal fixation technique involves immobilizing the spine using orthopedic stabilizing rods, commonly referred to as spine rods, which are positioned generally parallel to the spine. This may be accomplished by exposing the spine posteriorly and fastening bone screws to the pedicles of vertebral bodies. The pedicle screws are generally placed two per vertebra and serve as anchor points for the spine rods. Coupling elements or implants adapted for receiving a spine rod therethrough are then used to join the spine rods to the pedicle screws. A set screw or fastener then fastens the spine rod into a seat in a coupling element.

Instruments are utilized for inserting a spine rod into position within an orthopedic device such as a coupling element. Surgeons have encountered considerable difficulty when attempting to use these instruments to insert a spine rod into the seat of the coupling element and then inserting a fastener to secure the set up. For example, U.S. Pat. No. 5,910,141 to Morrison provides a rod introduction apparatus capable of laterally aligning a rod with an implant and vertically advancing the rod into position in the implant. The instrument, however, is difficult to use since it requires two hands, one hand to hold the instrument while it clamps the implant and one hand to operate the lateral alignment and vertical alignment means to properly position the rod in the implant.

In addition, U.S. Pat. No. 5,020,519 to Hayes et al. discloses an instrument for seating a spine rod into a hook. The instrument grips the hook with teeth and clamps the hook between the jaws. The thumb wheel must be rotated to shift the pusher thereby urging the spine rod into the hook. Again, it is difficult to utilize this instrument with a single hand.

There remains a need for improved instruments for urging or persuading spinal rods into position in orthopedic devices such as coupling elements or implants. In particular, there remains a need for spinal rod persuaders that may be effectively utilized with one hand. Moreover, there is a need for a simple design that both holds the coupling element stationary while persuading the rod into position. There is a further need for a rod persuader that locks as the rod is advanced into position. It is advantageous for a rod persuader to be easily removed from gripping the coupling element after the rod is properly positioned. It is further advantageous to provide a cannula in the rod persuader in which a set screw or other fastener may be inserted and delivered to the coupling element while the rod persuader is gripping the coupling element and rod.

SUMMARY OF THE INVENTION

According to one aspect of the invention, a rod persuader or an apparatus for urging an orthopedic or spinal rod into a recess or seat on an orthopedic device such as an implant, coupling element, or pedicle screw system is provided. The apparatus includes a body that is releasably attachable to the orthopedic device, pusher member and a trigger slidingly coupling the pusher member to the body.

The trigger may be actuated to translate the pusher member into contact with the rod and continue translating the pusher member until the rod is urged into recess of the orthopedic device. The pusher bar comprises a slide coupled to the body via the trigger and a sleeve attached to the slide so that the slide and sleeve translate together. Additionally, the sleeve includes at least one pusher bar integral with the sleeve and for accommodating the rod upon contact. Furthermore, the rod persuader may include a grip extending from the body and a handle extending from the trigger so that the rod persuader may be comfortably held in one hand. The handle is movable toward the grip to actuate the trigger.

According to another aspect of the invention, the rod persuader has a pair of fingers extending from an end of the body. The fingers are adaptable to releasably grip the orthopedic device. The fingers are elastic members that are separable to receive and grip the orthopedic device therebetween. The fingers may further include projections that cooperate with recess on the orthopedic device that allows the rod persuader to snap onto the orthopedic device. Additionally, the sleeve may include portions such as arms that prevent the fingers of the body from separating while gripping the orthopedic device as the sleeve is advanced.

According to another aspect of the invention, the rod persuader defines a cannula for receiving a fastener and a driver to secure the rod to the orthopedic device. The body and/or the pusher member may have channels which together form the cannula.

According to another aspect of the invention, a rod persuader or apparatus for urging and securing an orthopedic rod to an orthopedic device is provided. The apparatus includes a body releasably attachable to the orthopedic device, a pusher member coupled to the body via a trigger, and a ratchet. Actuation of the trigger translates the pusher member into contact with the rod and urges the rod into the recess of the orthopedic device, the ratchet controls the translation of the pusher member in steps so that after each step, the ratchet locks into position to prevent the pusher member from reverting backwards.

The pusher member comprises a slide slidingly coupled to the body, a sleeve attached to the slide, and at least one pusher bar integral with the slide. A grip may extend from the body and a handle may extend from the trigger. An elastic member is operatively associated with the grip and handle to hold the handle in a normally open position so that moving the handle toward the grip actuates the trigger to advance the ratchet. Thus, the elastic member locks the ratchet in position at each step. According to another aspect of the invention, the ratchet is attached to the handle or the grip. The ratchet comprises a rack having a plurality of female teeth. Each of the teeth on the rack corresponds to one step of the ratchet. The rack further includes a hinge connecting the rack to the grip or the handle and a male tooth extending opposite the female teeth from the handle or the grip and cooperating with the female teeth. Thus, as the handle is moved toward the grip, the male tooth is advanced to the first female tooth and locked into position. The male tooth advances along the rack of the female teeth each time the handle is moved and the male tooth locks in at each step. As this occurs, the pusher member translates in steps to urge the rod into position. The ratchet is unlocked by rotating the rack about the hinge.

According to yet another aspect of the invention, the ratchet comprises a plurality of female teeth defined in the pusher member or the body and a male tooth extending opposite the female teeth from the body or the pusher member. Moving the handle, thus actuates the trigger to translate the pusher member and advance the male tooth along the female teeth, step-by-step, locking in at each step. A tab extends from the body and is operable to unlock the ratchet. In one aspect of the invention, the pusher member includes a slide coupled to the body via the trigger, a sleeve attached to the slide, and at least one pusher bar for direct contact with the rod.

In accordance with another aspect of the invention, the body may further include a pair of fingers for releasably gripping the orthopedic device. The sleeve includes portions such as a pair of arms for preventing the fingers of the body from separating while holding the orthopedic device when the sleeve is translated. The rod persuader also includes a cannula formed by the channels of the slide and body. The pusher bar further defines a recess for accommodating the rod.

According to yet another aspect of the invention, an apparatus for securing a spinal rod to a pedicle screw is provided. The apparatus includes a generally longitudinally body defining a channel, a generally longitudinal pusher member defining a channel, a cannula formed by the channels, a ratchet, a grip extending from the body, a trigger slidingly coupling the pusher member to the body, a handle extending from the trigger, and a handle extending from the body. The handle is movable toward the grip to actuate the trigger and thereby translate the pusher member toward the spinal rod and into contact therewith. The ratchet controls the translation of the pusher member and rod in steps, locking at each step. An elastic member is associated with the grip and handle to return the handle back to a normally open position after it has been moved.

The apparatus may further include a pair of elastic fingers extending from the body that are separable to receive and grip the pedicle screw. The pusher member may include a slide attached to the body via the trigger, a sleeve and at least one pusher bar. The sleeve may include a pair of arms extending therefrom for preventing the fingers from separating.

According to another aspect of the invention, the ratchet includes a plurality of female teeth and a male tooth. The female teeth may be defined on a rack attached to the handle or grip via a hinge, or the female teeth may be defined in the slide or the body. Accordingly, the male tooth extends opposite the female teeth at the grip or handle, or the male tooth is defined opposite the female teeth in the body or slide.

According to yet another aspect of the invention, a method for securing an orthopedic rod to an orthopedic device using a rod persuader including a body having a grip extending therefrom, a pusher member and a trigger coupling the pusher member to the body and having a handle extending therefrom is provided. The method includes the steps of holding the rod persuader in a single hand, engaging the orthopedic device via a pair of fingers extending from the body, displacing the handle toward the grip to actuate the trigger and thereby advance the pusher member, contacting the rod with the pusher member, displacing the handle further to advance the rod into the seat of the orthopedic device, securing the rod to the orthopedic device and releasing the rod persuader from the orthopedic device.

In accordance with another aspect of the invention, the engagement of the orthopedic device further includes contacting the fingers of the body with the orthopedic device and applying a force to the body to separate the fingers allowing for insertion of the orthopedic device between the fingers. The securing step further includes inserting a fastener into the cannula and using a driver to tighten the fastener to secure the rod to the orthopedic device.

According to another aspect, the method further includes removing the driver and removing the apparatus from the orthopedic device by applying a force to the body away from the orthopedic device.

In accordance with another aspect of the invention, a method for securing a rod to an orthopedic device is provided. The method utilizes a rod persuader including a body with a grip, a pusher member, a trigger with a handle, a ratchet, and an elastic member connecting the handle to the grip. The method includes holding the rod persuader in a single hand, engaging the orthopedic device via fingers on the body, displacing the handle to actuate the trigger and advance the ratchet one step, and thereby translate the pusher member, locking the ratchet in position at the step, and repeatedly displacing the handle to advance the rod into position step by step.

The engaging step may include contacting the fingers with the orthopedic device and applying a force to the body to separate the fingers to allow for insertion of the orthopedic device there between.

According to another aspect, the securing step includes inserting a fastener into the cannula and using a driver to tighten the fastener to secure the rod to an orthopedic device. Finally, the rod persuader is released from the orthopedic device by unlocking the ratchet and applying a force to the body away from the orthopedic device to separate the fingers thereby releasing the rod persuader.

The method may further include inserting a fastener into the cannula and using a driver to tighten the fastener to secure the rod to the orthopedic device.

BRIEF DESCRIPTION OF THE DRAWINGS

FIG. FIG.1B is a front perspective view of the instrument of FIG. 1A in the closed position.

DETAILED DESCRIPTION

Figure 1A:
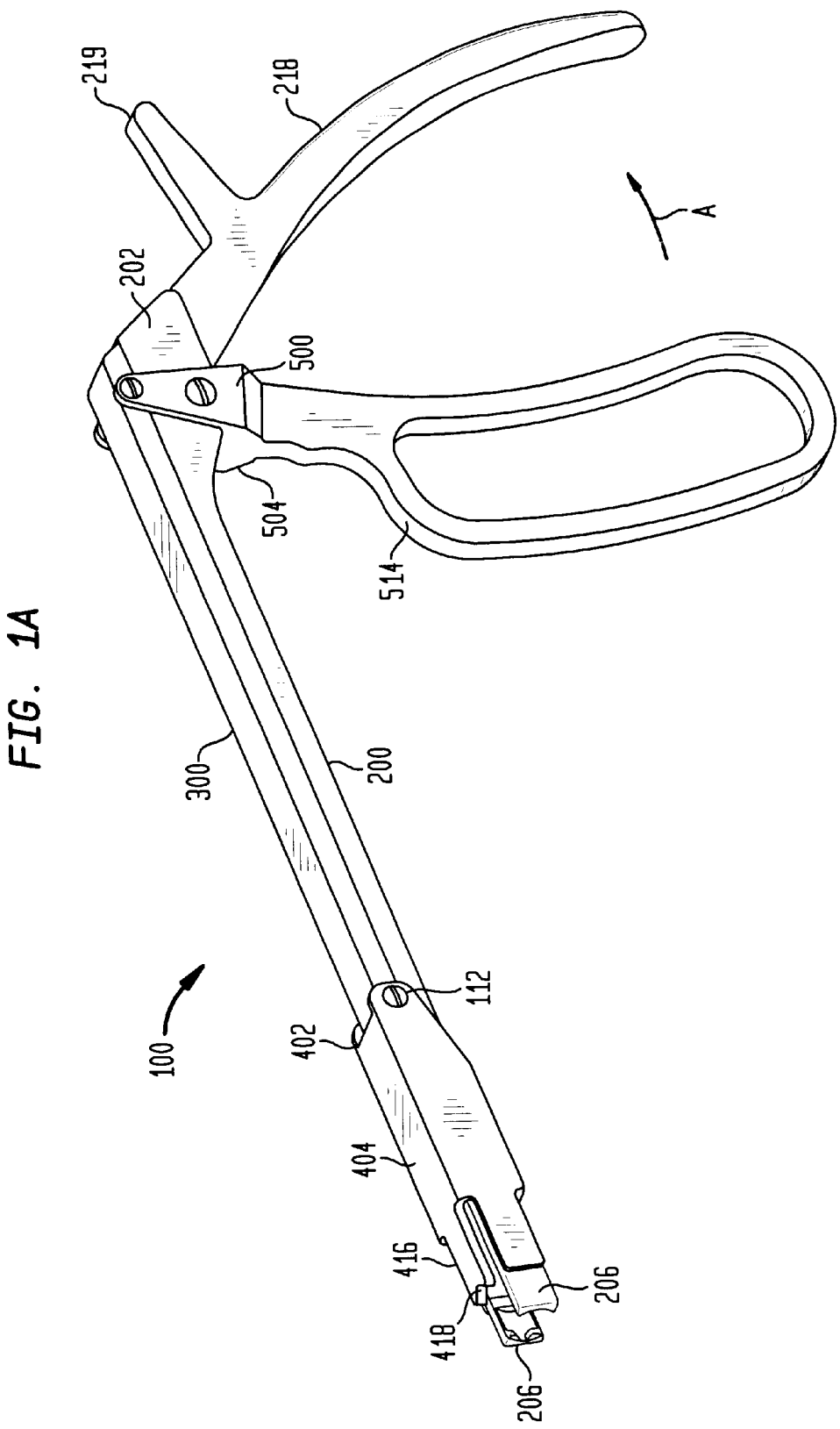
FIG. 1A is a front perspective view of an instrument for urging a spinal rod in the open position in accordance with the present invention.
Figure 1C:
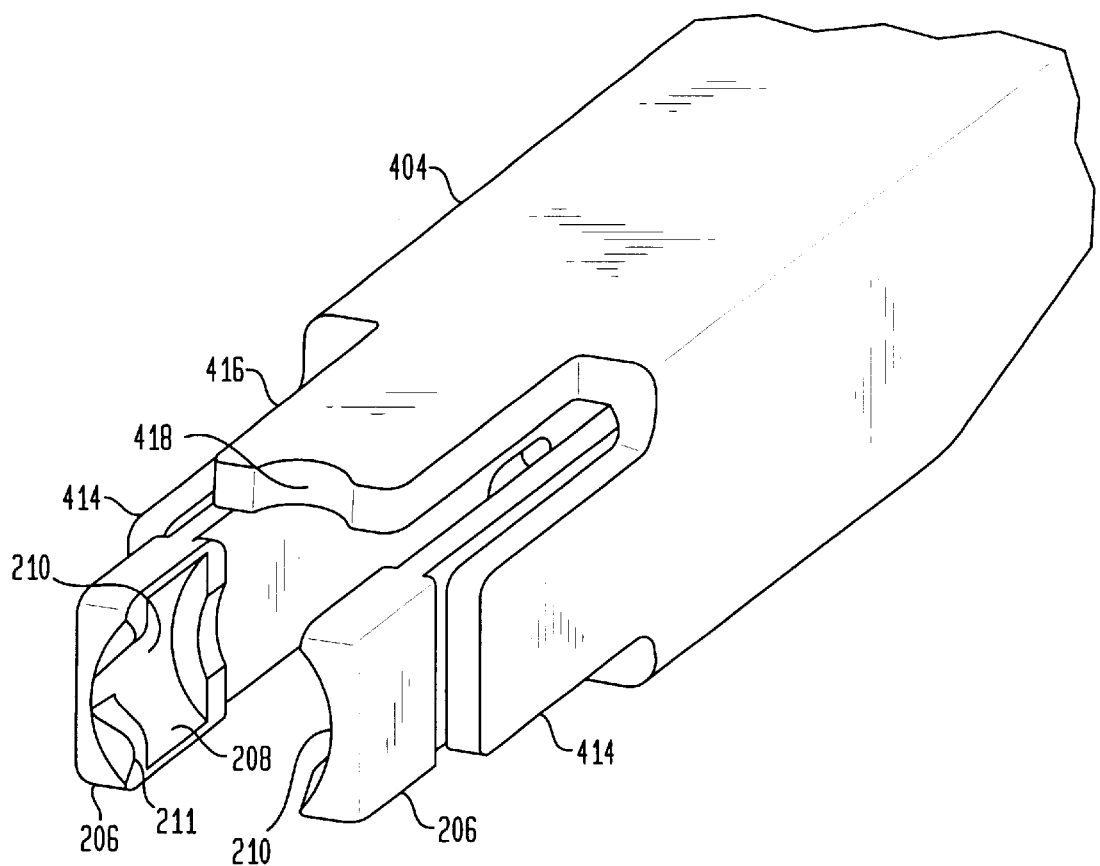
FIG. 1C is a front perspective close-up view of section C—C of FIG. 1A.

FIGS. 1A though 1D show an instrument for persuading a rod into 114 a seator recess 102 of an orthopedic device or a coupling element 104. The instrument comprises a generally longitudinal body 200, a slide 300, a sleeve 400 and a trigger 500, each illustrated separately in FIGS. 2, 3, 4, and 5 respectively. The slide 300 and sleeve 400 together form a pusher member.

Figure 1D:
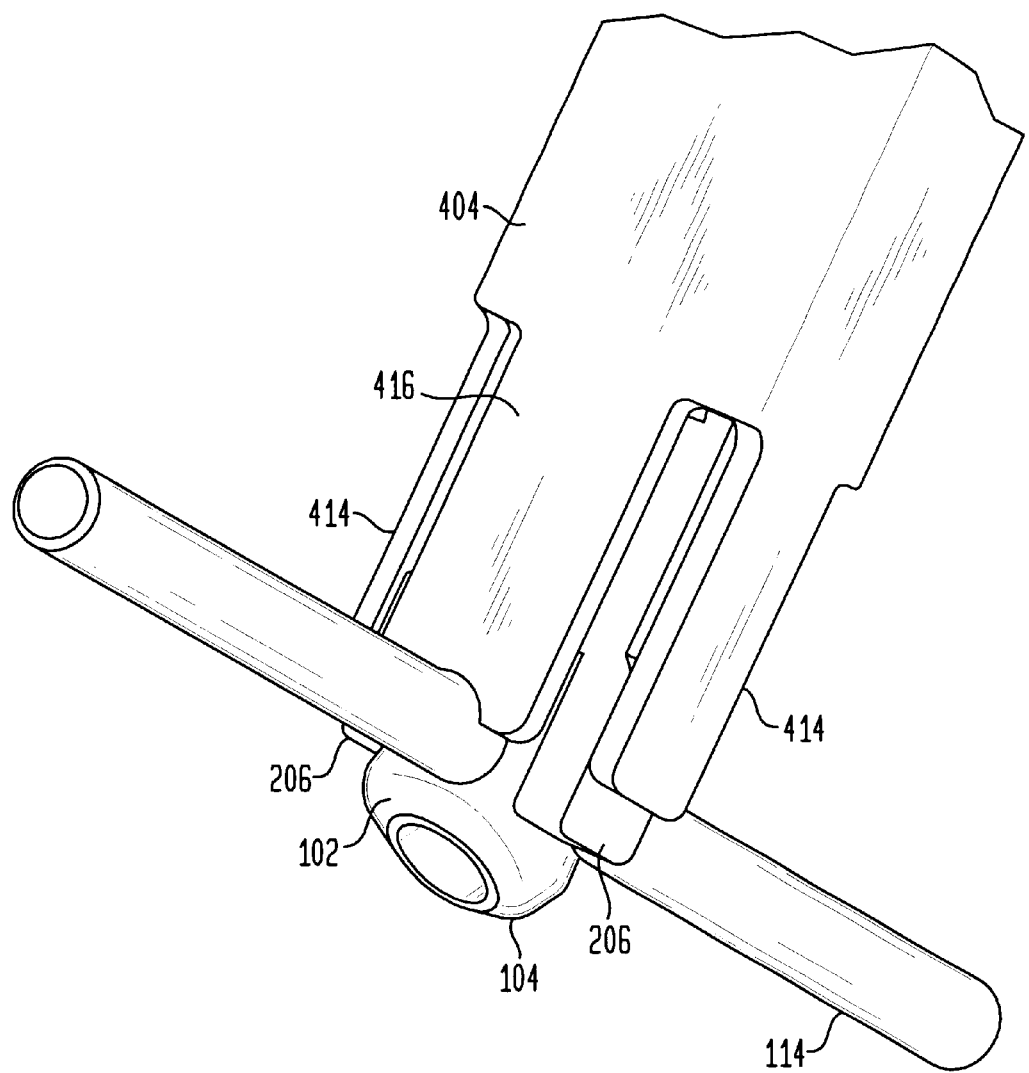
FIG. 1D is a top perspective close-up view of the sleeve, arms, rod and orthopedic device in accordance with the present invention.
Figure 1E:
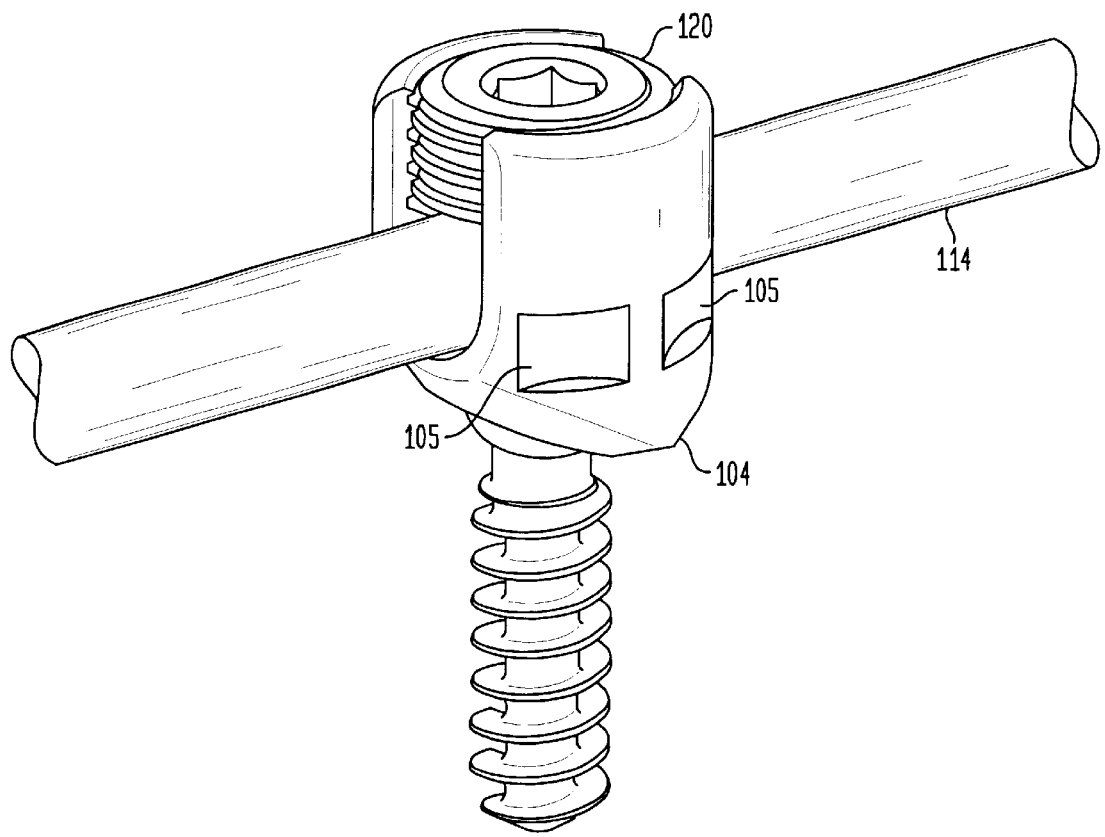
FIG. 1E is a front perspective view of the rod fully secured to the orthopedic device.
Figure 2:
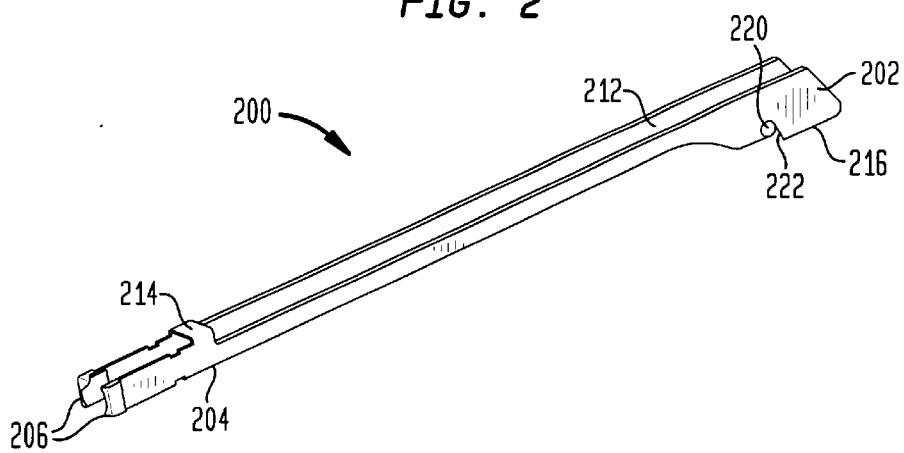
FIG. 2 is a front perspective view of a body in accordance with the present invention.
Figure 3:
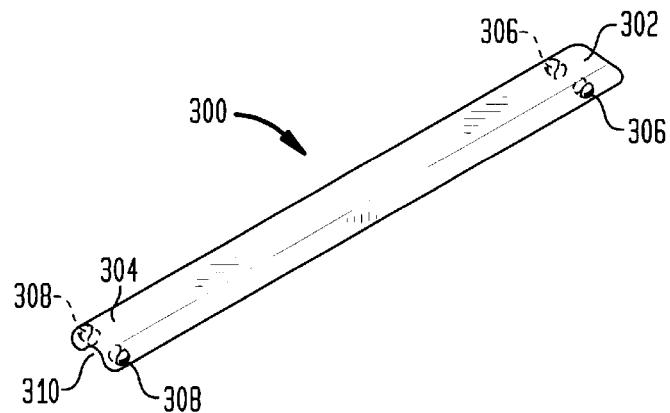
FIG. 3 is a front perspective view of a slide in accordance with the present invention.
Figure 4:
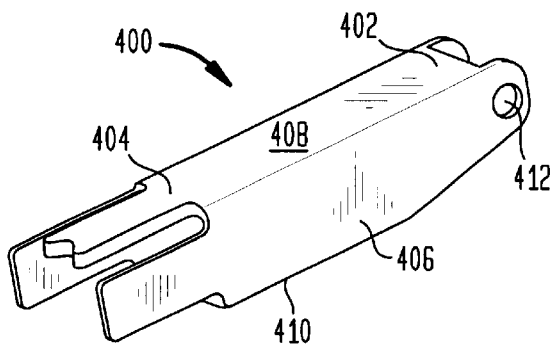
FIG. 4 is a front perspective view of a sleeve in accordance with the present invention.
Figure 5:
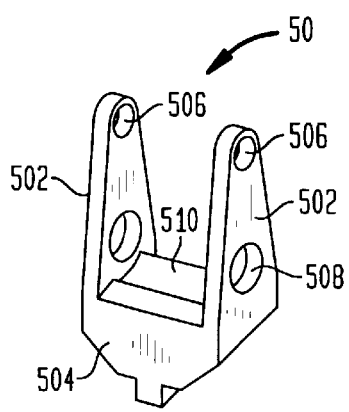
FIG. 5 is a front perspective view of a trigger in accordance with the present invention.

Referring now to FIGS. 1A–1E and 2, the body 200 defines a first end 202 and a second end 204. A pair of fingers 206 extend from the second end 204 of the body 200. The fingers 206 each have an interior wall 208 which define indentations 210 and notches 211 that correspond to the shape of the coupling element 104. As shown in FIG. 1E, the coupling element 104 defines grooves 105 for receiving notches 211. The fingers are rigid, but also elastic so that they act in a springing motion so that the application of a force will separate the fingers. Thus, a force may be applied to the body in order to insert the coupling element 104 between the fingers 206, as shown in FIG. 1D. Once in position, the fingers 206 securely grip the coupling element 104 via the grooves 105 by the spring motion.

The body 200 further defines a channel 212 extending longitudinally on its top side from the first end 202 through the middle area of the body. The channel 212 ends at an abutment 214 located at the second end 204. The abutment 214 projects vertically higher than the first end 202 of the body. The fingers 206 extend longitudinally from opposite sides of the abutment 214.

In a preferred embodiment a joint 216 is provided extending at an angle from the second end 204. A pistol grip 218 with thumb rest 219 may be attached to the second end 204 at the joint 216 via welding, bolting or any other method of attaching. In an alternate embodiment, the grip 218 and the body 200 may be integral and therefore the body 200 and grip 218 would be formed of a single piece. The body 200 further defines a pair of threaded holes 220 to receive screws 106. A notch 222 extends downwards from the area of the holes 220.

Referring now to FIGS. 1A–D and 3, the slide 300 has a first end 302 and a second end 304. The first end defines a pair of threaded holes 306 and the second end defines a pair of threaded holes 308. The slide 300 further defines a channel 310 extending longitudinally on its bottom side along the entire length of the slide.

FIGS. 1A–1D and 4 show the sleeve 402. The sleeve 400 is generally shaped like a square column defining a first end 402 and a second end 404 and having a pair of opposite sides 406, a top side 408 and a bottom side 410. The first end 402 defines holes 412 on either side 406 of the sleeve 400. A pair of arms 414 extend longitudinally from opposite sides 406 at the second end 404 of the sleeve 400. A pusher bar 416 extends longitudinally from the top side 408 of the sleeve 400, between the arms 414. The pusher bar 416 defines a groove 418 for accommodating the spine rod.

FIGS. 1A–1D and 5 show the trigger 500 having a pair of branches 502 and a bottom piece 504 connecting the branches 502. Each branch defines an upper hole 506 and a lower hole 508. The inside surface of the bottom piece 504 has an indentation 510. The outside surface of the bottom piece 504 also defines a joint 512 extending therefrom. In a preferred embodiment, a handle 514 is attached to the trigger at the joint 512 via welding, bolting or any other method of attaching. In addition, the handle 514 and trigger 500 may be integral so that the handle 514 and trigger 500 together are formed of a single piece.

As illustrated in the FIGS., the instrument 100 comprises the body 200, the slide 300, the sleeve 400 and the trigger 500. The trigger 500 connects the slide 300 to the body 200, so that the slide and body are generally parallel. The notch 222 at the first end 202 of the body fits into the indentation 510 of the trigger 500. Lower holes 508 of the trigger are generally aligned with threaded holes 220 of the body. Screws 106 secure the trigger 500 to the body 200 via the holes 508, 220.

Upper holes 506 of the trigger are generally aligned with threaded holes 306 of the slide. Screws 108 secure the trigger 500 to the slide 300 via holes 506, 306. Thus, the slide 300 fits on top of the body 200 and extends the length from the first side 202 of the body 200 to a point just past the middle of the body 200. There is room for the slide to advance longitudinally forward on top of the body toward the abutment 214 of the body. The channel 212 of the body 200 and the channel 310 of the slide 300 together form a cannula 110.

The holes 412 of the sleeve 400 are generally aligned with the threaded holes 308 at the second end 304 of the sleeve 300. Thus, the sleeve 400 is attached to the second end of the slide 300 via screws 112. Moreover, the sleeve 400 partially encases the second end 204 of the body 200 which assists coupling the sleeve 400 and slide 300 to the body 200. The arms 414 of the sleeve 400 partially extend adjacent to the exterior walls of the fingers 206.

In operation, a user (not shown) grasps the instrument in one hand at the pistol grip 218 and handle 514. The coupling element 104 having a spine rod resting within or nearby the seat 102 is engaged or gripped between the fingers 206 of the body 200 by applying a small force allowing the fingers 206 to separate slightly and then grasp the coupling element 104 via the groove 105 as shown in FIG. 1D. The handle 514 is then displaced, moved or squeezed toward the grip 218 in the direction of arrow A as shown in FIGS. 1A and 1B. The displacement of the handle 514 causes the sleeve 400 to advance toward the rod 114 and coupling element 104. Squeezing the handle 514 angularly displaces the trigger 500 moving the notch 222 of the body 200 out of the locked position from the indentation 510 of the trigger 500. Thus, with a single continuous squeeze of the handle, the pusher bar 416 contacts the rod 114 at groove 418. The rod 114 is then advanced into the recess or seat 102 of the coupling element 104 to the position shown in FIG. 1D, while the fingers 206 continue to grip the coupling element 104. As the slide 300 and sleeve 400 advance, the arms 414 of the sleeve also advance adjacent to the fingers 206. Thus, the arms 206 prevent the fingers 206 from separating. The user of the instrument may then continuously squeeze the handle to maintain the positioning of the rod 114 on the seat 102 of the coupling element. While the positioning is maintained, the user may use the free hand to perform other tasks. In addition, a fastener 120 (FIG. 1E) may be inserted through the cannula 110 to secure the rod 114 to the coupling element 104. A driver (not shown) may also be inserted through the cannula to tighten the fastener. Once the rod is secured, the user may release the handle allowing the pusher to withdraw from contact with the rod. Then, the instrument release its grip on the coupling element 104 by slightly rotating the instrument to displace the ratches 211 from the groove 105 of the coupling element and to slightly separate the fingers 206. A force may then be applied on the instrument in the direction opposite the coupling element. This force will free the instrument from its grip on the coupling element 104. Thus, the rod 114 is secured to the coupling element 104 as shown in FIG. 1E.

Figure 6A:
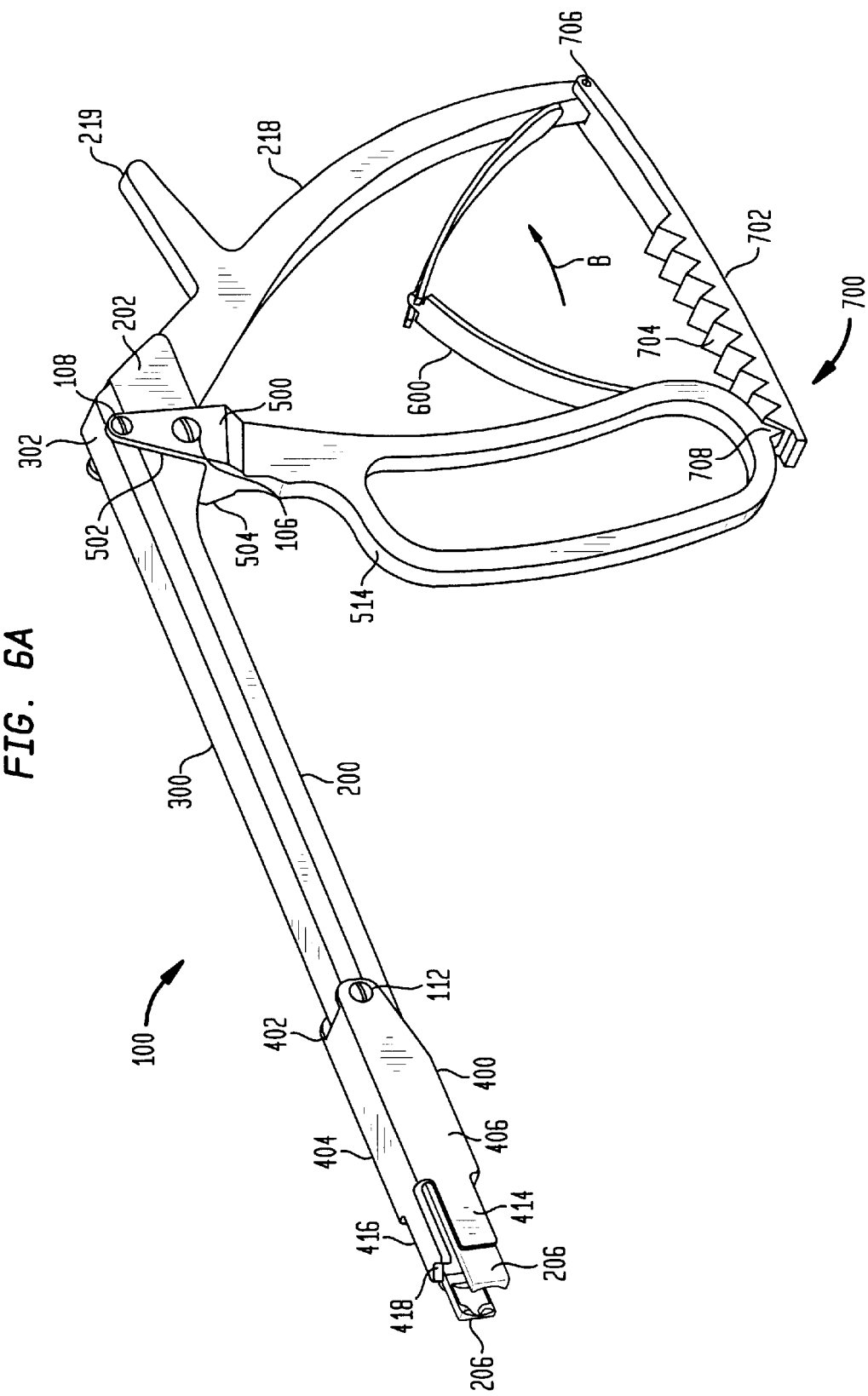
FIG. 6A is a front perspective view of another embodiment of the invention, showing an instrument for urging a rod with a ratchet in the open position.
Figure 6B:
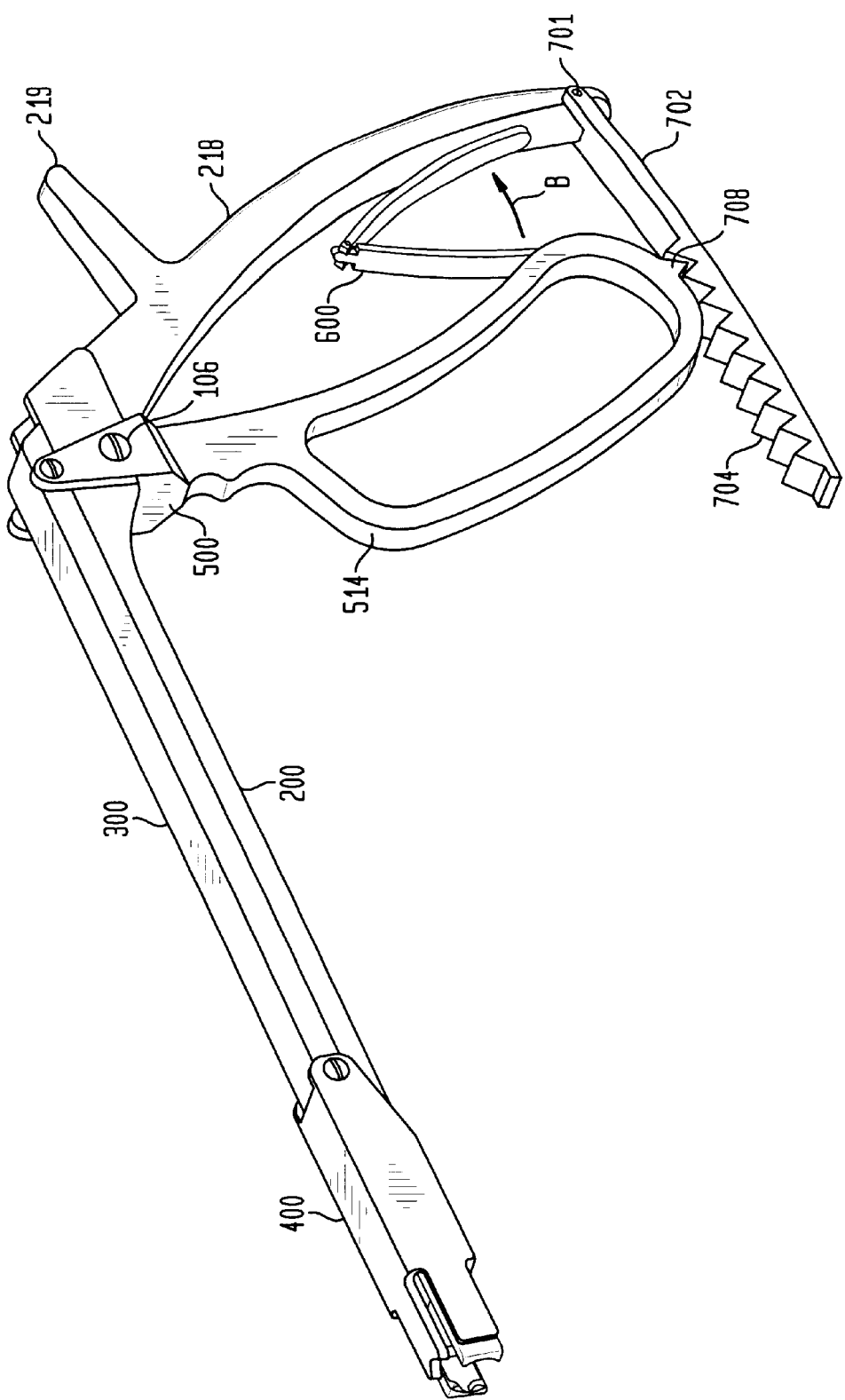
FIG. 6B is a front perspective view of the instrument of FIG. 6A in the closed position.

Referring now to FIGS. 6A and 6B, another embodiment of the invention is shown where like elements are similarly numbered. The instrument further comprises a ratchet mechanism 700 and a springing connector 600 connecting the handle 514 and grip 218. The ratchet mechanism includes a rack 702 having a plurality of female teeth 704. The rack 702 is connected to the bottom of the pistol grip at hinge 706. A male tooth 708 extends from the bottom of the handle 514.

The male tooth 708 of the handle cooperates with the female teeth 704 of the rack 702. FIG. 6A shows the instrument in the beginning or open position so that the male tooth is resting at a first end 710 of the rack 702. Each of the female teeth of the rack represents a single step.

In operation, the user grasps the instrument with one hand via the pistol grip 218 and the handle 514. After the instrument grips the coupling element via the notches 211 of the fingers, the user then squeezes the handle 214 toward the pistol grip in the direction of arrow B to displace the male tooth 708 one step into the first female tooth. The springing connector 600 causes the handle to lock in this first step, advancing the slide and the sleeve forward the distance of one step. The user repeatedly squeezes the handle to displace the male tooth a single step at a time into each of the female teeth. As this occurs, the slide 300 and sleeve 400 advance forward so that the pusher 416 contacts the rod 114 at groove 418 and urges the rod into position in the seat 102 of the coupling element 104 as illustrated in FIG. 1D at each step.

As the ratchet mechanism is operated, the springing connector 600 locks the male tooth. Thus, the user does not have to constantly apply pressure to the handle in order to maintain the position of the rod. Rather, the locking nature of the ratchet maintains the advancement of the slide and sleeve and in turn, the advancement of the rod. Additionally, the user may release his grasp on the instrument without threat of the rod 114 regressing back away from the coupling element 104, since the ratchet is locked in position.

Once again, after the rod 114 is positioned in the seat 102 of the coupling element 104, a fastener 120 may be inserted through the cannula. A driver may be used through the cannula to tighten the fastener to secure the rod 114 to the coupling element 104. Once the rod is secured, the rack 702 of the ratchet mechanism may be rotated about the hinge 706 in the direction of arrow C, to unlock the ratchet mechanism. This results in the pusher 416 releasing its contact with the rod 114. The instrument may then be removed from its grip on the coupling element as discussed above.

Figure 7A:
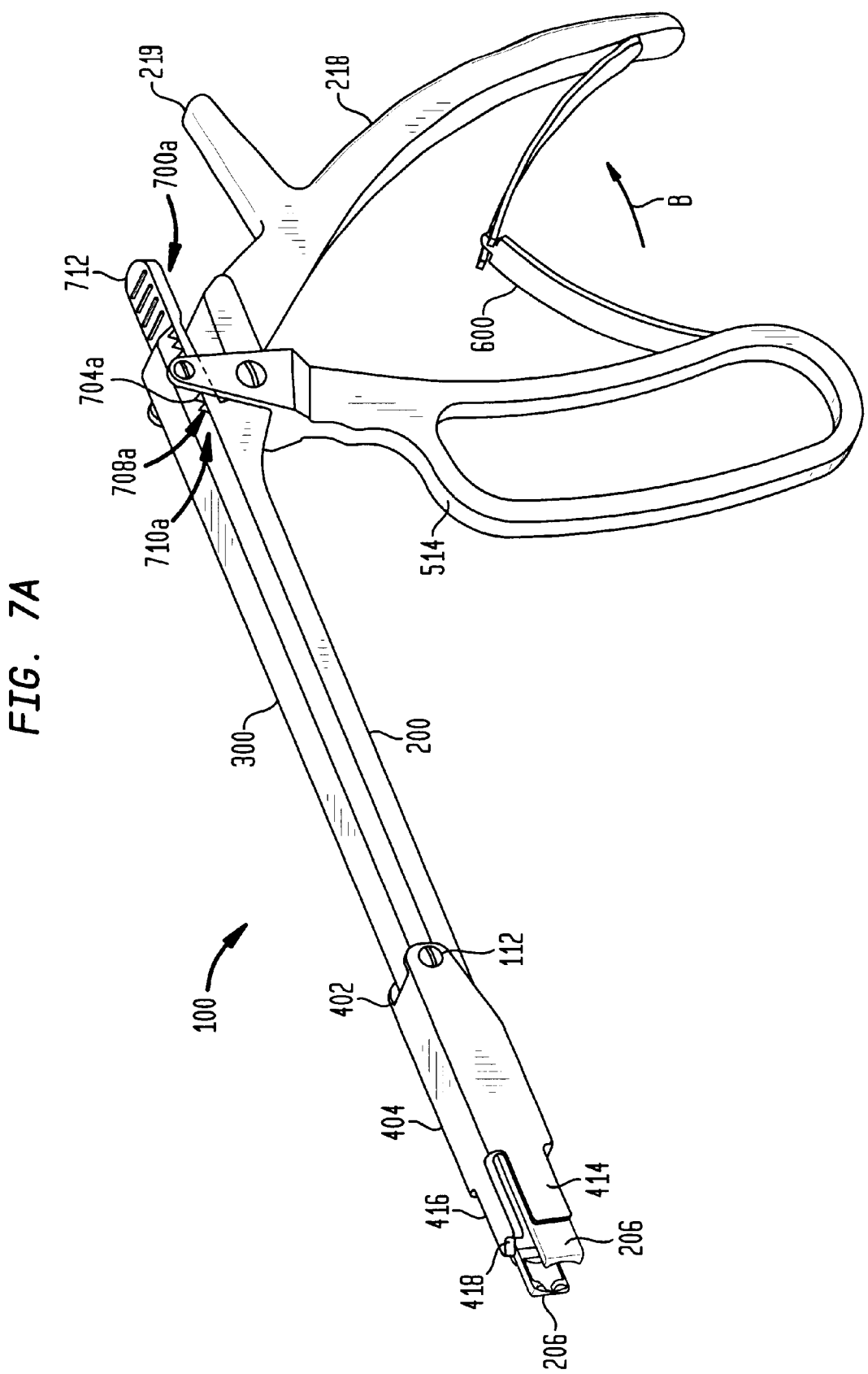
FIG. 7A is a front perspective view of another embodiment of the invention, showing an instrument for urging a rod with a ratchet in the open position.
Figure 7B:
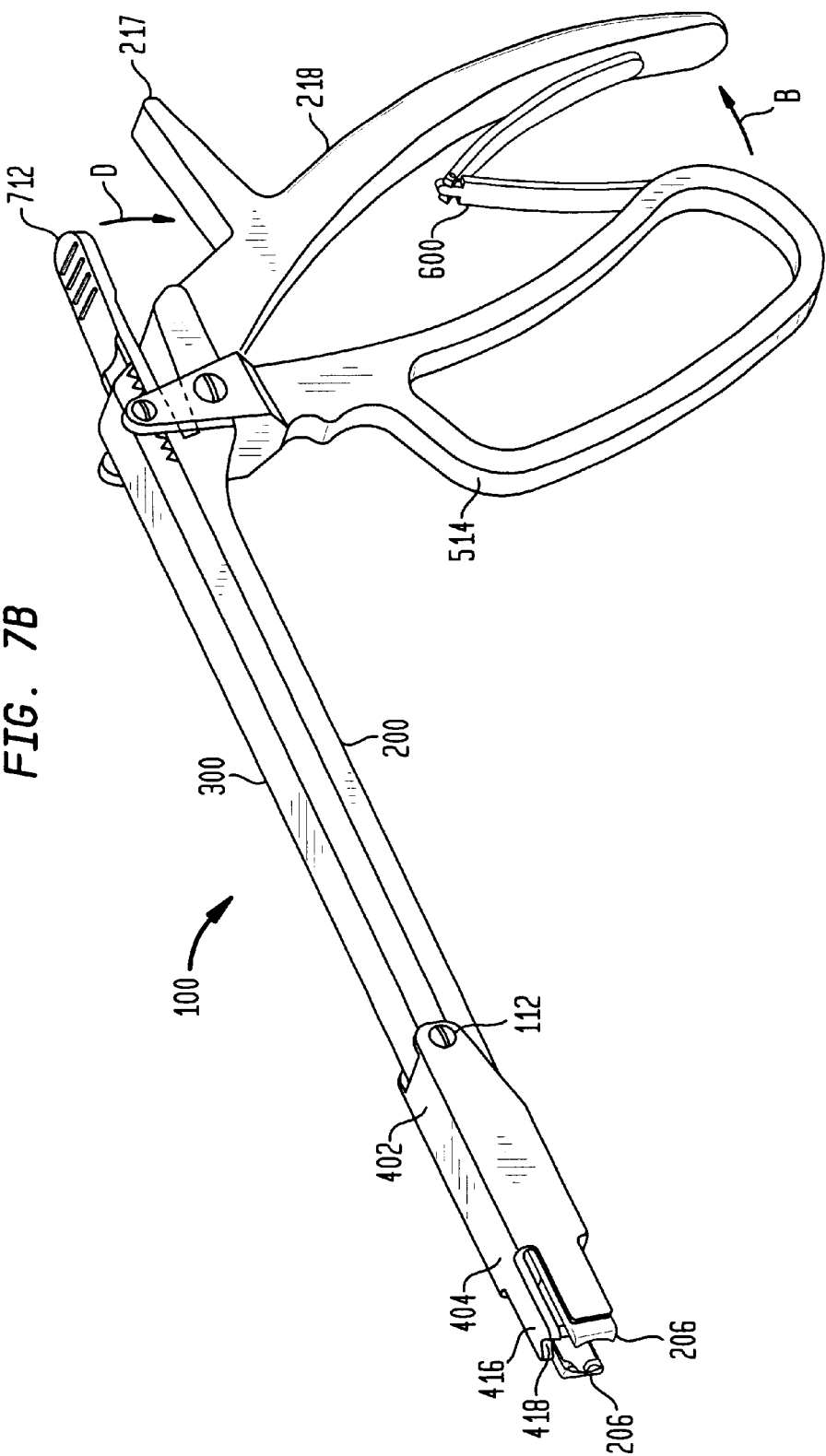
FIG. 7B is a front perspective view of the instrument of FIG. 7A in the closed position.

FIGS. 7A and 7B show yet another embodiment of the invention where like elements are similarly numbered. In this embodiment, the instrument generally comprises a body 200, slide 300, sleeve 400, trigger 500, springing connector 600 and a ratchet mechanism 700a.

The ratchet mechanism 700a includes a plurality a female teeth 704a defined in the bottom of the slide 300. A male tooth 708a extends upwards from the body 200. In addition, a tab 712 extends from the body 200. The male tooth 708a of the body cooperates with the female teeth 704a of the slide.

FIG. 7A shows the instrument in the beginning or open position so that the male tooth is resting at a front end 710a of the plurality of female teeth 704a. Each of the female teeth 704a represents a single step.

In operation, the user grasps the instrument with one hand via the pistol grip 218 and the handle 514. After the instrument grips the coupling element via the notches 211 of the fingers, the user then squeezes the handle 214 toward the pistol grip in the direction of arrow B which displaces the male tooth 708 one step into the first female tooth 704. The springing connector 600 causes the male tooth to lock in this first step, advancing the slide 300 and the sleeve 400 forward the distance of one step. The user repeatedly squeezes the handle to displace the male tooth a single step at a time and lock into position at each of the female teeth. As this occurs, the slide 300 and sleeve 400 advance forward so that the pusher 416 contacts the rod 114 at groove 418 and urges the rod into position in the seat 102 of the coupling element 104 as illustrated in FIG. 1D.

As the ratchet mechanism is operated, the springing connector 600 locks the male tooth at each step. Thus, the user does not have to constantly apply pressure to the pressure in order to maintain the position of the rod. Rather, the locking nature of the ratchet maintains the advancement of the slide and sleeve and in turn, the advancement of the rod. Additionally, the user may release his grasp on the instrument without threat of the rod 114 regressing back away from the coupling element 104, since the ratchet is locked in position.

Once again, after the rod 114 is positioned in the seat 102 of the coupling element 104, a fastener 120 may be inserted through the cannula. A driver may be used through the cannula to tighten the fastener to secure the rod 114 to the coupling element 104. Once the rod is secured, the tab 712 of the ratchet mechanism may be rotated in the direction of arrow D, to unlock the ratchet mechanism. This results in the pusher 416 releasing its contact with the rod 114. The instrument may then be removed from its grip on the coupling element 104 as discussed above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. An apparatus for urging an orthopedic rod into a recess of an orthopedic device, comprising:
   a body having a first end and a second end, said second end being releasably attachable to the orthopedic device;
   a pusher member;
   a trigger coupling said pusher member to said body, wherein actuation of said trigger translates said pusher member toward said second end into contact with the orthopedic rod and further urges the orthopedic rod into the recess of the orthopedic device.

2. An apparatus according to claim 1, wherein said pusher member comprises:
   a slide slidingly coupled to said body via said trigger;
   a sleeve attached to said slide and partially surrounding said second end; and
   at least one pusher bar integral with said sleeve and defining a recess for accommodating the orthopedic rod upon contact.

3. An apparatus according to claim 1, further comprising:
   a grip extending angularly from said first end of said body; and
   a handle extending from said trigger, said handle being movable toward said grip to actuate said trigger and thereby, translate said pusher member toward said second end.

4. An apparatus according to claim 1, further comprising a pair of fingers extending from said second end for releasably gripping the orthopedic device.

5. An apparatus according to claim 4, wherein said fingers are elastic members that are separable to receive and grip the orthopedic device therebetween.

6. An apparatus according to claim 5, wherein said fingers define projections cooperable with recesses on the orthopedic device.

7. An apparatus according to claim 4, wherein said sleeve includes portions in juxtaposition with said fingers and upon translation of said pusher member toward said second end, said portions translate adjacent to said fingers to prevent said fingers from separating.

8. An apparatus according to claim 7, wherein said portions comprise a pair of arms extending from opposite sides of said sleeve.

9. An apparatus according to claim 1, further comprising a cannula extending from said first end of said body to said second end of said body.

10. An apparatus according to claim 9, wherein said cannula is formed by channels in said body and said pusher member that are arranged one on top of the other.

11. An apparatus for urging an orthopedic rod into a recess of an orthopedic device, comprising:
    a body having a first end and a second end, said second end being releasably attachable to the orthopedic device;
    a pusher member slidingly coupled to said body; and
    a trigger coupling said pusher member to said body, wherein actuation of said trigger translates said pusher member toward said second end into contact with the orthopedic rod and further urges the orthopedic rod into the recess of the orthopedic device;
    a ratchet for controlling the translation of said pusher member in steps, wherein said ratchet locks at each step to prevent the pusher member from translating away from the orthopedic rod.

12. An apparatus according to claim 11, wherein said pusher member comprises:
    a slide slidingly coupled to said body via said trigger;
    a sleeve attached to said slide and partially surrounding said second end; and
    at least one pusher bar integral with said sleeve and defining a recess for accommodating the orthopedic rod upon contact.

13. An apparatus according to claim 11, further comprising:
    a grip extending angularly from said first end of said body;
    a handle extending from said trigger, said handle being movable toward said grip to actuate said trigger and thereby, translate said pusher member toward said second end, wherein moving said handle advances said ratchet one step; and
    an elastic member operatively associated with said handle and said grip to hold said handle in a normally open position, wherein said elastic member locks said ratchet at each step after said handle is moved.

14. An apparatus according to claim 13, wherein said ratchet is attached to said grip or said handle.

15. An apparatus according to claim 14, wherein said ratchet comprises:
    a rack including a plurality of female teeth, each said female tooth being one step;
    a hinge attaching said rack to said grip or said handle, wherein said rack may be rotated about said hinge to unlock said ratchet; and
    a male tooth extending opposite said female teeth from said handle or said grip and cooperating with said female teeth, wherein moving said handle advances said male tooth into the next said female tooth and said elastic member locks said male tooth at the next step.

16. An apparatus according to claim 15, further comprising a pair of fingers extending from said second end for releasably gripping the orthopedic device.

17. An apparatus according to claim 16, wherein said fingers are elastic members that are separable to receive and grip the orthopedic device therebetween.

18. An apparatus according to claim 17, wherein said fingers define projections cooperable with recesses on the orthopedic device.

19. An apparatus according to claim 16, wherein said sleeve includes portions in juxtaposition with said fingers and upon translation of said pusher member toward said second end, said portions translate adjacent to said fingers to prevent said fingers from separating.

20. An apparatus according to claim 19, wherein said portions comprise a pair of arms.

21. An apparatus according to claim 14, further comprising a cannula extending from said first end of said body to said second end of said body.

22. An apparatus according to claim 21, wherein said cannula is formed by channels in said body and said pusher member that are arranged one on top of the other.

23. An apparatus according to claim 13, wherein said ratchet is formed at said first end of said body.

24. An apparatus according to claim 23 wherein said ratchet comprises:
    a plurality of female teeth defined in a bottom of said pusher member or a top of said body, each said female tooth being one step;
    a male tooth extending opposite said female teeth from said top of said body or said bottom of said pusher member and cooperating with said female teeth, wherein moving of said handle advances said male tooth into the next said female tooth and said elastic member locks said male tooth at the next step; and a tab extending from said body, wherein said tab is operable to unlock said ratchet.

25. An apparatus according to claim 24, further comprising a pair of fingers extending from said second end for releasably gripping the orthopedic device.

26. An apparatus according to claim 16, wherein said fingers are elastic members that are separable to receive and grip the orthopedic device therebetween.

27. An apparatus according to claim 26, wherein said fingers define projections cooperable with recesses on the orthopedic device.

28. An apparatus according to claim 26, wherein said sleeve includes portions in juxtaposition with said fingers and upon translation of said pusher member toward said second end, said portions translate adjacent to said fingers to prevent said fingers from separating.

29. An apparatus according to claim 11, further comprising a cannula extending from said first end of said body to said second end of said body.

30. An apparatus according to claim 29, wherein said cannula is formed by channels in said body and said pusher member that are arranged one on top of the other.

31. An apparatus according to claim 23, further comprising a cannula extending from said first end of said body to said second end of said body.

32. An apparatus for securing a spinal rod to a pedicle screw, comprising:

a generally longitudinal body defining a channel on a top side, said body being capable to releasably grip the pedicle screw;

a generally longitudinal pusher member adjacent to said body and defining a channel on a bottom side, said channel of said body and said channel of said slide forming a cannula being capable of receiving a fastener for securing the spinal rod to the pedicle screw and a driver for tightening the fastener;

a trigger slidingly coupling said pusher member to said body, wherein actuation of said trigger translates said slide toward and into contact with the spinal rod and further urges the spinal rod into a recess of the pedicle screw;

a ratchet for controlling the translation of said pusher member in steps;

a grip extending angularly from an end of said body;

a handle extending from said trigger, said handle being movable toward said grip to actuate said trigger and thereby, translate said pusher member toward the spinal rod; and an elastic member operatively associated with said handle and said grip to hold said handle in a normally open position, wherein said elastic member locks said ratchet at each step.

33. An apparatus according to claim 32, further comprising:

a pair of elastic fingers extending from said body, said elastic fingers being separable to receive and grip the pedicle screw therebetween; and wherein said pusher member comprises:

a slide slidingly coupled to said body via said trigger;

a sleeve attached to said slide and including a pair of arms in juxtaposition with said finger, wherein upon translation of said pusher member, said arms translate adjacent to said fingers to prevent said fingers from separating; and at least one pusher bar integral with said sleeve and defining a recess for accommodating the spinal rod upon contact.

34. An apparatus according to claim 33, wherein said ratchet comprises:

a rack including a plurality of female teeth, each said female tooth being one step;

a hinge attaching said rack to said grip or said handle, wherein said rack may be rotated about said hinge to unlock said ratchet; and a male tooth extending from said handle or said grip and cooperating with said female teeth, wherein moving said handle advances said male tooth into the next said female tooth and said elastic member locks said male tooth at the next step.

35. An apparatus according to claim 33 wherein said ratchet comprises:

a plurality of female teeth defined in a bottom of said slide or a top of said body, each said female tooth being one step;

a male tooth extending opposite said female teeth from said top of said body or said bottom of said slide and cooperating with said female teeth, wherein moving said handle advances said male tooth into the next said female tooth and said elastic member locks said male tooth at the next step; and a tab extending from said body, said tab being operable to unlock said ratchet.

36. A method for securing an orthopedic rod to an orthopedic device using a rod persuader including a body having a grip extending therefrom, a pusher member, and a trigger coupling said pusher member to said body and having a handle extending therefrom, said method comprising the steps of:

holding the rod persuader in a single hand at the grip and handle;

engaging the orthopedic device via a pair of fingers extending from the body;

displacing the handle toward the grip to actuate the trigger and thereby translating the pusher member toward the engaged orthopedic device;

contacting the rod with the pusher member while the handle is displaced;

displacing the handle further to advance the rod into the seat of the orthopedic device;

securing the rod to the orthopedic device; and releasing the rod persuader from the orthopedic device.

37. A method according to claim 36, wherein said step of engaging further comprises the steps of:

contacting the fingers of the body with the orthopedic device; and applying a force to the body to separate the fingers thereby allowing for insertion of the orthopedic device therebetween.

38. A method according to claim 37, wherein said step of securing further comprises the steps of:

inserting a fastener into a cannula formed between the pusher member and the body;

inserting a driver into the cannula; and tightening the fastener via the driver to secure the rod to the orthopedic device.

39. A method according to claim 38, wherein said step of releasing further comprises the steps of:
removing the driver from the cannula;
rotating the body to separate the fingers; and
applying a force to the body away from the orthopedic device to release the rod persuader from the orthopedic device.

40. A method for securing an orthopedic rod to an orthopedic device using a rod persuader including a body having a grip extending therefrom, a pusher member, a trigger coupling the pusher member to the body and having a handle extending therefrom, a ratchet, and an elastic member attaching the handle to the grip, said method comprising:
holding the rod persuader in a single hand at the grip and handle;
engaging the orthopedic device via a pair of fingers extending from the body;
displacing the handle to actuate the trigger and advance the ratchet one step, and thereby translate the pusher member toward the engaged orthopedic device; and
locking the ratchet in position at the one step;
repeating said displacing step and said locking step until the pusher member contacts the orthopedic rod and the orthopedic rod is translated into the seat of the orthopedic device; and
securing the orthopedic rod to the orthopedic device.

41. A method according to claim 40, wherein said step of engaging further comprises the steps of:
contacting the fingers of the body with the orthopedic device; and
applying a force to the body thereby allowing for insertion of the orthopedic device therebetween.

42. A method according to claim 41, wherein said securing step further comprises the steps of:
inserting a fastener into a cannula formed between the pusher member and the body;
inserting a driver into said cannula; and
tightening the fastener via the driver to secure the rod to the orthopedic device.

43. A method according to claim 42, wherein said step of releasing further comprises the steps of:
removing the driver from the cannula;
unlocking the ratchet;
rotating the body to separate the fingers; and
applying a force to the body away from the orthopedic device to release the rod persuader from the orthopedic device.

44. An apparatus for urging an orthopedic rod toward an orthopedic device, comprising:
a body having a first end and a second end, said second end being releasably attachable to said orthopedic device and adapted to receive a portion of said orthopedic rod;
a pusher member; and
a triggering mechanism coupled to said pusher member and said body,
wherein said triggering mechanism is operable to urge said orthopedic rod toward said orthopedic device, and
wherein displacement of said triggering mechanism occurs in a direction substantially parallel to a direction of advancement of said orthopedic rod toward said orthopedic device.

45. The apparatus of claim 44, wherein said triggering mechanism comprises a pistol grip fixedly attached to said body at said first end, and a trigger coupled to said pusher member and said body.

46. The apparatus of claim 45, wherein said trigger is pivotally hinged to said pusher member and said body.

47. The apparatus of claim 46, wherein a portion of said trigger has a fixed distance between a first pivot point connecting said trigger to said body and a second pivot point connecting said trigger to said pusher member.

48. The apparatus of claim 44, wherein said pusher member comprises a slide and a sleeve, and
wherein said slide has a first end and a second end, is pivotally coupled to said triggering mechanism at said first end, and is pivotally coupled to said sleeve at said second end.

49. The apparatus of claim 48, wherein a portion of said sleeve defines a recess for accommodating said orthopedic rod.

50. The apparatus of claim 44, further comprising a set of fingers extending from said second end of said body for releasably gripping said orthopedic device.

51. The apparatus of claim 50, wherein said set of fingers are elastic, and separable to receive and grip said orthopedic device therebetween.

52. The apparatus of claim 44, further comprising a cannula extending from said first end of said body to said second end of said body.

53. The apparatus of claim 52, wherein said cannula is formed by channels in said body and said pusher member.

54. The apparatus of claim 44, further comprising a ratchet for controlling advancement of said pusher member.

55. The apparatus of claim 54, wherein said ratchet is located at said first end of said body.

56. The apparatus of claim 54, wherein said ratchet is located at said triggering mechanism.

57. An apparatus for urging an orthopedic rod toward an orthopedic device, comprising:
a body having a first end and a second end, said second end being releasably attachable to said orthopedic device and adapted to receive a portion of said orthopedic rod;
a pusher member;
a pistol grip fixedly attached to said body at said first end, and
a trigger coupled to said pusher member and said body,
wherein said trigger is operable to urge said orthopedic rod toward said orthopedic device when said trigger is displaced toward said pistol grip.

58. The apparatus of claim 57, wherein said trigger is pivotally hinged to said pusher member and said body.

59. The apparatus of claim 58, wherein a portion of said trigger has a fixed distance between a first pivot point connecting said trigger to said body and a second pivot point connecting said trigger to said pusher member.

60. The apparatus of claim 57, wherein said trigger includes a handle portion.

61. The apparatus of claim 57, wherein said pusher member comprises a slide and a sleeve, and
wherein said slide has a first end and a second end, is pivotally coupled to said trigger at said first end, and is pivotally coupled to said sleeve at said second end.

62. The apparatus of claim 61, wherein a portion of said sleeve defines a recess for accommodating said orthopedic rod.

63. The apparatus of claim 57, further comprising a set of fingers extending from said second end of said body for releasably gripping said orthopedic device.

64. The apparatus of claim 63, wherein said set of fingers are elastic, and separable to receive and grip said orthopedic device therebetween.

65. The apparatus of claim 57, further comprising a cannula extending from said first end of said body to said second end of said body.

66. The apparatus of claim 65, wherein said cannula is formed by channels in said body and said pusher member.

67. The apparatus of claim 57, further comprising a ratchet for controlling advancement of said pusher member.

68. The apparatus of claim 67, wherein said ratchet is located at said first end of said body.

69. The apparatus of claim 67, wherein said ratchet is located at said pistol grip and cooperates with said trigger.

* * * * *

UNITED STATES PATENT AND TRADEMARK OFFICE
CERTIFICATE OF CORRECTION

PATENT NO.     : 6,660,006 B2                                         Page 1 of 1
DATED          : December 9, 2003
INVENTOR(S)    : Aaron Markworth and Yves Crozet It is certified that error appears in the above-identified patent and that said Letters Patent is hereby corrected as shown below:

Column 5,
Line 31, after "instrument" insert -- 100 --.

Signed and Sealed this

Twenty-fourth Day of February, 2004

JON W. DUDAS
*Acting Director of the United States Patent and Trademark Office*